(12) United States Patent
Hummel et al.

(10) Patent No.: US 8,948,563 B2
(45) Date of Patent: Feb. 3, 2015

(54) MINIATURIZED ON-LINE TRACE ANALYSIS

(75) Inventors: Helmut Hummel, Schierling (DE);
Alfred Lechner, Lappersdorf (DE)

(73) Assignee: Hochscule Regensburg, University of Applied Science, Regensburg (DE)

( * ) Notice: Subject to any disclaimer, the term of this patent is extended or adjusted under 35 U.S.C. 154(b) by 400 days.

(21) Appl. No.: 13/500,792

(22) PCT Filed: Oct. 5, 2010

(86) PCT No.: PCT/EP2010/064833
§ 371 (c)(1),
(2), (4) Date: Jun. 27, 2012

(87) PCT Pub. No.: WO2011/042439
PCT Pub. Date: Apr. 14, 2011

(65) Prior Publication Data
US 2012/0257193 A1    Oct. 11, 2012

(30) Foreign Application Priority Data
Oct. 6, 2009  (DE) .......................... 10 2009 048 384

(51) Int. Cl.
*G02B 6/10* (2006.01)
*G01N 21/05* (2006.01)
*B01F 13/00* (2006.01)
(Continued)

(52) U.S. Cl.
CPC ............ *G01N 21/05* (2013.01); *B01F 13/0066* (2013.01); *B01L 3/502707* (2013.01); *G01N 21/31* (2013.01); *G01N 21/645* (2013.01); *G01N 21/78* (2013.01); *B01L 2300/0867* (2013.01); *G01N 2021/0346* (2013.01); *G01N 2021/0378* (2013.01); *G01N 2021/056* (2013.01); *G01N 2021/058* (2013.01);
(Continued)

(58) Field of Classification Search
None
See application file for complete search history.

(56) References Cited

U.S. PATENT DOCUMENTS 5,444,807 A    8/1995  Liu
5,690,763 A *  11/1997 Ashmead et al. ............... 156/60
(Continued)

FOREIGN PATENT DOCUMENTS

DE    1002005 028 166 A1    6/2005
EP          1 182 443 A2     2/2002
(Continued)

OTHER PUBLICATIONS

Datta, Arindom et al., "Microfabrication and Characterization of Teflon AF-Coated Liquid Core Waveguide Channels in Silicon", IEEE Sensors Journal, vol. 3, No. 6, Dec. 2003, pp. 788-795.
(Continued)

*Primary Examiner* — Tina Wong

(57) ABSTRACT

The invention relates to a measuring apparatus comprising an apparatus for forming a liquid optical waveguide having a substrate (1) having an at least partially curved closed microchannel (2) having a low-refractive coating (13), whereby there is formed in the substrate (1) at least one feed line (6) for supplying liquid, and whereby there is provided at least at one end of the closed microchannel (2) an apparatus for coupling light axially into the closed microchannel and/or for coupling light axially out of the closed microchannel (2), further comprising a light source (4), a light detector (5), and a first liquid pump (9) which supplies a sample liquid (7) to the closed microchannel (2) via the at least one feed line (6, 6*a*).

16 Claims, 5 Drawing Sheets

Figure 1:
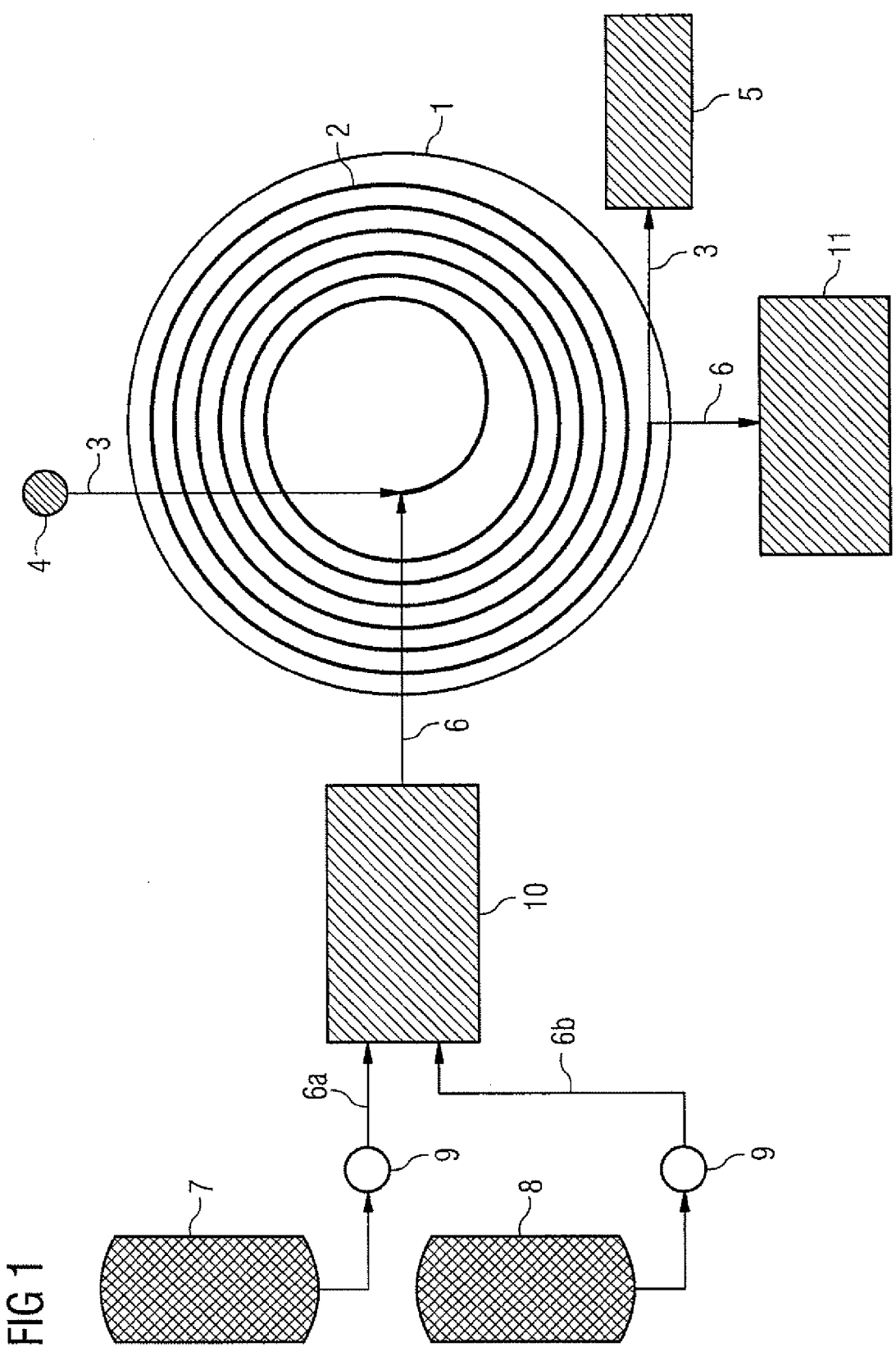

(51) Int. Cl.
*B01L 3/00* (2006.01)
*G01N 21/31* (2006.01)
*G01N 21/64* (2006.01)
*G01N 21/78* (2006.01)
*G01N 21/03* (2006.01)

(52) U.S. Cl.
CPC .................. *G01N 2021/6467* (2013.01); *G01N 2021/6482* (2013.01); *G01N 2201/08* (2013.01)
USPC ........................................................ 385/146

(56) References Cited

U.S. PATENT DOCUMENTS

| | | | |
|---|---|---|---|
| 6,246,825 | B1 | 6/2001 | Kershaw |
| 6,385,380 | B1 | 5/2002 | Friedrich et al. |
| 2003/0022506 | A1 | 1/2003 | Schwab et al. |
| 2005/0129580 | A1* | 6/2005 | Swinehart et al. ............ 422/100 |
| 2007/0165980 | A1 | 7/2007 | Jenkins et al. |
| 2007/0263477 | A1 | 11/2007 | Sudarsan et al. |
| 2008/0317423 | A1* | 12/2008 | Stepanov et al. ............. 385/132 |
| 2010/0314327 | A1* | 12/2010 | Lean et al. .................... 210/738 |
| 2012/0257193 | A1* | 10/2012 | Hummel et al. ............. 356/73.1 |

FOREIGN PATENT DOCUMENTS

| | | |
|---|---|---|
| WO | 99/57584 | 11/1999 |
| WO | WO99/57584 A1 | 11/1999 |

OTHER PUBLICATIONS

Jiang, Linan et al., "Integrated waveguide with a microfluidic channel in spiral geometry for spectroscopic applications", Applied Physics Letters, vol. 90, Issue 11, Mar. 14, 2007, Abstract Only.

Hawkins, Aaron R., et al., "Optofluidic waveguides: II. Fabrication and structures", NIH, Jul. 19, 2007, pp. 1/1-18/1.

Hawkins, Aaron R., et al., "Optofluidic waveguides: I. concepts and implementations", NIH, Jan. 1, 2008, pp. 1/1-17/1.

Grosse, Axel et al., "Deep wet etching of fused silica glass for hollow capillary optical leaky waveguides in microfluidic devices", Journal of Micromechanics & Microengineering, vol. 11, No. 3, May 1, 2001, pp. 257-262.

Fouckhardt, H. et al., "Micro flow modules with combined fluid flow channel and optical detection waveguide—hyper Rayleigh scattering as a case study", Fresenius' Journal of Analytical Chemistry, vol. 371, No. 2, Sep. 1, 2001, pp. 218-227.

Datta, Arindom, et al., "Microfabrication and characterization of teflon af-coated liquid core waveguide channels in silicon", IEEE Sensors Journal, vol. 3, No. 6, Dec. 1, 2003, pp. 788-795.

Jiang, Linen et al, "Integrated waveguide with a microfluidic channel in spiral geometry for spectroscopic applications", Applied Physics Letters, vol. 90, No. 11, Mar. 14, 2007, pp. 111108-111108.

Hawkins, Aaron R., et al., "Optofluidic waveguides: II. Fabrication and structures", vol. 4, No. 1-2, Jul. 19, 2007, pp. 17-32.

* cited by examiner

MINIATURIZED ON-LINE TRACE ANALYSIS

CROSS REFERENCE TO RELATED APPLICATIONS

This application claims priority from PCT/EP2010/064833, filed Oct. 5, 2010 and German Application No. 10 2009 048 384.5, filed Oct. 6, 2009.

This invention relates to an apparatus and a method for spectroscopic measurement of substances dissolved in liquids. The invention relates further to a method for manufacturing such an apparatus.

In environmental analysis, in particular in water analysis, the detection and measurement of substances dissolved in liquids in low concentrations plays a great role. In this connection, different spectroscopic methods such as absorption, transmission, fluorescence and Raman are known. For this purpose, liquids are analyzed for example in cuvettes or cells consisting of optically transparent, light-conducting material, for example quartz glass. To lower the detection limit of the substances to be detected, it is known to realize light paths as long as possible within the liquid in which the substance to be detected is dissolved. For this purpose, there are used for example elongate cuvettes, capillaries or also liquid optical waveguides in which the light losses occurring along the long light path are reduced by a totally reflective inside or outside coating. The refractive index of the totally reflective coating here must be smaller than the refractive index of the liquid, usually water, in the liquid optical waveguide. Water possesses a refractive index of n=1.33. For forming a liquid waveguide for aqueous solutions there can therefore be used inside coatings of amorphous, fluorinated polymers such as for example Teflon AF 1600 or Teflon AF 2400 with refractive indices of 1.29 and 1.31 or also inorganic layer materials, such as nanoporous silica films and silicon dioxides with refractive indices as low as 1.18 or magnesium fluoride-magnesium oxyhydroxide mixed layers with refractive indices as low as 1.09. The stated refractive indices relate to the wavelength of the sodium D line.

For realizing the above-mentioned long light paths there are typically used liquid optical waveguides with lengths in the range of several meters. This leads to considerable dimensions of the resulting detection apparatus, a consequence being that the intended detection measurements can frequently only be carried out in the laboratory, whereas a prompt detection of such trace substances on site is desirable for example directly on a body of water to be analyzed. The dimensions of known apparatuses, however, prevent such an on-site use, or at least make it considerably more difficult.

Alternative measuring methods not requiring long light paths, such as for example atomic absorption spectroscopy (AAS), the employment of an inductively coupled plasma mass spectrometer (ICPMS) and ion chromatography likewise involve very large and cost-intensive devices.

The object of the present invention is to state a miniaturized measuring apparatus that nevertheless creates a long light path within the liquid to be analyzed, a manufacturing method for such a measuring apparatus as well as a corresponding measuring method.

The invention is based on the finding that, contrary to hitherto known configurations, a liquid optical waveguide need not possess a circular cross section, where the cross section is the area of the hollow space to be filled with liquid that results upon a section perpendicular to the longitudinal direction of the liquid optical waveguide. In other words, a light conduction also takes place when the cross section of the liquid optical waveguide deviates from the known circular shape. Based on this finding is the idea underlying the present invention to provide the liquid optical waveguide, not as a self-supporting element, but as a closed microchannel on a suitable substrate. A self-supporting liquid optical waveguide for the purposes of the present print is an elongate hollow body that is coated on the inside for forming a liquid optical waveguide and consists of a material that is sufficiently stable mechanically so that no further elements for stabilization are necessary. Such a self-supporting liquid optical waveguide only needs to be mounted at individual, spaced points.

Accordingly, the measuring apparatus of the invention comprises an apparatus for forming a liquid optical waveguide. The latter comprises a substrate having an at least partially curved microchannel. After corresponding lining with a low-refractive coating, after provision of a suitable cover and after filling with liquid, the microchannel forms the liquid optical waveguide. Through the at least partially curved forming of the microchannel, an accordingly curved liquid optical waveguide is realized on the substrate. Thus, the length of the liquid optical waveguide is not limited by the outer dimensions of the substrate, as is the case with straight microchannels. Rather, the microchannel can be provided for example with a multiplicity of loops or windings on the substrate surface, making it possible to realize a long microchannel, and thus an accordingly long liquid optical waveguide, despite small dimensions of the substrate.

The microchannel is preferably of spiral-shaped configuration, whereby the center of the spiral coincides at least substantially with the center of the circular disk. Particularly preferably, it is an Archimedean spiral, wherein the radius of the spiral arm, that is, of the microchannel, is proportional to the azimuthal angle. For the purposes of the present print, the term "spiral-shaped" is understood to refer to a shape that has at least one complete revolution around a center and whose radius around this center changes monotonically, preferably proportionally to the azimuthal angle. The preferred spiral-shaped configuration of the microchannel has the advantage that a multiplicity of closely neighboring windings can be provided on the substrate surface. Preferably, neighboring windings have a mutual spacing between 800 and 1500 µm, preferably 800, 900, 1000, 1200 or 1500 µm. Thus, a great percentage area of the substrate surface can be provided for forming the microchannel, thereby making it possible to realize a great length of the microchannel and an accordingly long light path in the liquid optical waveguide to be created. Moreover, the curvature of the microchannel, that is, the change of the longitudinal direction along the longitudinal direction, changes continuously and monotonically, preferably linearly, thereby maximizing the radius of curvature at each point of the microchannel, avoiding small radii of curvature and thus minimizing the flow resistance for the liquid within the liquid optical waveguide to be formed. The monotonic course of the curvature of the microchannel and of the corresponding liquid optical waveguide further has the decisive advantage that only a minimum number of loss modes occurs upon the light conduction, thereby maximizing the light conductivity of the liquid optical waveguide to be formed. Preferably, the minimum radius of curvature of the optionally spiral-shaped microchannel amounts to 20 mm, 10 mm or 5 mm.

The microchannel preferably has a depth in the range between 50 and 500 µm, in particular 200, 250, 300, 400 or 500 µm, whereby each of the stated single values can represent a boundary of the stated values range. With such dimensions of the microchannel, a laminar liquid flow can be realized in good approximation in the later liquid optical waveguide, meaning that turbulences in the liquid that disturb the spectroscopic analysis are avoided. Further, the microchannel has an altogether small total volume despite a great channel length because of the small channel cross section, so that the minimum amount of a sample liquid to be analyzed is small. The channel lengths preferably amount to more than 1, 2, 3, 5, 10, 15, 20, 25 or 30 meters.

The low-refractive coating of the apparatus for forming a liquid optical waveguide according to the invention possesses a thickness of 2 to 10 µm, in particular 2, 3, 4, 5 or 10 µm, whereby the stated single values can represent boundaries of the stated values range. Preferably, the coating consists of Teflon, nanoporous silicon dioxide or a nanoporous double compound of magnesium fluoride-magnesium oxyhydroxide.

In the apparatus for forming a liquid optical waveguide according to the invention, there is formed in the substrate a feed line which permits a supplying and removing of liquid into the closed microchannel and out of the closed microchannel. Preferably there is formed at each end of the microchannel a respective feed line, one of which supplies the liquid to the closed microchannel and the other of which removes the liquid from the closed microchannel. Thus, the liquid in the liquid optical waveguide can be easily replaced and in particular a continuous liquid stream can also be provided during the spectroscopic measurement, by for example the liquid being pumped through the microchannel during the spectroscopic measurement, which can be realized by a liquid pump that is in operation during the spectroscopic measurement. It is advantageous here when a laminar flow is present within the liquid optical waveguide and turbulences in the liquid that disturb the spectroscopic analysis are avoided. This is obtained according to the invention by the feed lines extending non-axially with respect to the longitudinal directions of the microchannel and preferably forming an angle between 10 and 90 degrees, preferably 10, 15, 20, 30, 45, 60 or 90 degrees, with the longitudinal direction of the microchannel at the intersection point between feed line and microchannel. The stated single values can be boundaries of the stated values range.

Further, there is provided on the substrate at least one end of the closed microchannel, preferably at both ends of the closed microchannel, an apparatus for coupling light axially into the closed microchannel and/or out of the closed microchannel.

Preferably, the apparatus for axially coupling in and out is configured as a receiving means for an optical waveguide, whereby the receiving means forms an axial, straight continuation of the microchannel within the substrate. Through the semi-circular cross section of the microchannel, such an optical waveguide, in particular a single-mode optical waveguide, can be positioned suitably in the microchannel, in particular when the diameter of the optical waveguide is equal to the depth of the microchannel. Particularly preferably, there is provided in the microchannel between the closed microchannel provided as a liquid optical waveguide and the optical waveguide an element that guarantees an effective coupling of light in and/or out. This is preferably a microlens, in particular a GRIN (gradient-index) lens.

Alternatively, the apparatus for axially coupling light into and/or out of the closed microchannel can be configured as a deflecting unit which deflects light from the direction of the cover plate axially into the closed microchannel and/or light from the closed microchannel in the direction of the cover plate. This permits a coupling of light into and/or out of the closed microchannel even without an optical waveguide. The cover plate here has suitable gaps or is light-transmissive, which can be obtained for example by a cover plate of quartz glass. The deflecting unit can be for example a micromirror arranged in the substrate.

A light-transmissive, transparent cover plate, for example of quartz glass, has the advantage that the closed microchannel can thereby also be penetrated by radiation transversally. This is advantageous for example for fluorescence measurements and Raman measurements, as to be explained more closely below.

In a preferred embodiment of the apparatus for forming a liquid optical waveguide, a micromixer and/or a micropump is formed on the at least one liquid feed line of the substrate. This makes it possible, on the one hand, to further miniaturize the apparatus and also the resulting measuring apparatus. On the other hand, the provision of a micromixer permits the feed of two different liquids, thereby increasing the degree of freedom in designing the measuring method.

The measuring apparatus of the invention comprises, in addition to the described apparatus for forming a liquid optical waveguide, a light source, a light detector as well as a first liquid pump which supplies a sample liquid to the closed microchannel via the at least one feed line. The closed microchannel filled with the sample liquid forms a liquid optical waveguide. In the sample liquid the substance to be spectroscopically detected is present in dissolved form. The sample liquid is preferably an aqueous solution, that is, the refractive index of the sample liquid corresponds substantially to the refractive index of water. The light source here is adapted to penetrate the closed microchannel with light.

In a first embodiment of the measuring apparatus of the invention, the latter is adapted for carrying out transmission measurements or absorption measurements. For this purpose, the light of the light source is coupled axially into the closed microchannel or the liquid optical waveguide. This can be done via an optical waveguide. In this case, the cover plate can be light-non-transmissive and for example likewise be a silicon wafer. Alternatively, the axial coupling in of the light of the light source can also be realized by the above-described deflecting unit, whereby in this case the cover plate has suitable gaps and/or is light-transmissive. In basically analogous fashion, the transmitted light is supplied to the light detector at the other end of the microchannel, whereby this can again be done using an optical waveguide or a suitable deflecting unit.

Depending on the chosen measuring method, the light of the light source is monochromatic or broad-band and lies in the UV and/or visible (VIS) wavelength range. Likewise, the transmitted light can be supplied completely to the light detector, or it can be spectrally filtered or split, for example via wavelength filters or a spectrometric unit. Upon broad-band irradiation of light and subsequent spectral splitting of the transmitted light, the latter can be supplied to different light detectors, so that several measurements can be carried out in parallel at different wavelengths at the same time and thus different dissolved substances can be measured at the same time.

In a particularly preferred embodiment, the light source emits monochromatic light in the visible wavelength range, and the light detector detects the total transmitted light without previous spectral filtering. In a further preferred embodiment, the coupling in and out is effected via the above-mentioned deflecting units, so that the light source and the light detector can be arranged directly on the substrate or the cover plate of the apparatus for forming a liquid optical waveguide. For such an embodiment it is particularly suitable to use LED diodes or semiconductor laser diodes as a light source and photodiodes, for example avalanche photodiodes, as a light detector, which are available as components with small outer dimensions. This further miniaturizes the measuring apparatus of the invention. Avalanche photodiodes are highly sensitive and fast photodiodes that utilize the avalanche effect, which is also employed in Zener diodes.

In a further preferred embodiment, the cover plate of the apparatus for forming a liquid optical waveguide is light-transmissive and preferably formed of quartz glass and particularly preferably provided with a coating that is anti-reflective for the irradiated light, for example for UV light. Thus, light of the light source, which is preferably an excitation light source, can be irradiated through the cover plate transversally, that is, perpendicular to the longitudinal direction of the microchannel, whereby light is coupled into the liquid optical waveguide at high yield through the total or Fresnell reflection on the coated channel walls. This arrangement is suited for fluorescence measurements and Raman measurements, whereby the fluorescence light produced in the sample liquid is collected by the liquid optical waveguide and conducted to the ends of the liquid optical waveguide. In this embodiment, UV light is preferably irradiated and the fluorescence light coupled out axially and supplied to the light detector after optional spectral filtering. In so doing, one can dispense with a spectral filtering of the excitation light and thus a corresponding filter element, because the transversally irradiated excitation light has a great angle of incidence on the coating of the microchannel, so that no total reflection takes place. Accordingly, the excitation light is not conducted to the light detector through the liquid optical waveguide.

The measuring apparatus of the invention and the measuring method of the invention make it possible to detect many different substances by characteristic absorption bands in transmission measurements and absorption measurements. Depending on the substance to be detected, the light of the light source as well as a possible spectral filtering of the irradiated light are selected. For example, there can be detected organic solvents such as acetone, benzopyrene, benzene or anions such as nitrate or phosphate which have characteristic absorption bands in the near UV range. Likewise, there can be detected organic substances with a conjugated $\pi$ system which typically have absorption bands in the visible wavelength range. Likewise, $Ni^{2+}$ has a characteristic absorption band at 670 nm.

In the measuring apparatus of the invention, the liquid pump which supplies the sample liquid to the closed microchannel is preferably integrated as a micropump on the substrate of the apparatus for forming a liquid optical waveguide. This makes it possible to further miniaturize the measuring apparatus of the invention.

In a further preferred embodiment of the measuring apparatus, the latter is configured to also supply to the closed microchannel a second detection liquid besides the pump liquid. These two liquids are mixed before being passed into the closed microchannel, which is preferably done via a micromixer which is integrated in the substrate of the apparatus for forming a liquid optical waveguide. The detection liquid is supplied to the micromixer via a further liquid pump, whereby the mix ratio of sample liquid and detection liquid can be adjusted via the two liquid pumps. Preferably, both liquid pumps are integrated as micropumps on the substrate of the apparatus for forming a liquid optical waveguide, which further miniaturizes the measuring apparatus of the invention.

In a particularly preferred embodiment of the measuring method of the invention, metal ions are detected. A direct observation of such metal ions by means of absorption measurement is generally impossible, because metal ions typically have absorption bands in the low UV range. In a preferred embodiment of the measuring method of the invention, these metal ions trigger a detection reaction, whereby the product of the detection reaction can be detected via an absorption measurement. For this purpose, there is also supplied to the closed microchannel, besides the sample liquid containing the metal ions to be detected, a detection liquid in which a suitable complexing agent is dissolved. Upon mixture of the sample liquid and the detection liquid in the micromixer, the metal ions enter into coordination compounds with the complexing agent, whereby the resulting metal complexes have allowed charge-transfer transitions with high extinction coefficients $\epsilon$ which possess a strong absorption in the visible wavelength range. In this case, the detection of metal ions can advantageously be effected via the absorption of monochromatic visible light. A further spectral filtering before the light detector is advantageously unnecessary here.

In a first preferred embodiment of the measuring method, $Cu^{2+}$ ions are detected and the complexing agent employed is 1,10-phenanthroline ($C_{12}H_8N_2$). The resulting metal complex possesses an absorption at 650 nm. In a further preferred embodiment, $Fe^{2+}$ ions are detected which form, with 1,10-phenanthroline as a complexing agent, a metal complex which possesses an absorption at 510 nm. Likewise, $Fe^{2+}$ ions can be detected with 3-(2-pyridyl)-5,6-bis(4-phenyl-sulfonic acid)-1,2,4-triazine-5',5"-disodium salt ($C_{16}H_8N_4Na_2O_8S_2$) as a complexing agent, whereby the resulting complex shows an absorption at 567 nm.

A microchannel can in principle be provided in a substrate by different methods, for example by embossing polymers, such as polycarbonate, or milling. According to the invention, the microchannel is incorporated into the substrate by etching, preferably wet-chemical etching. For this purpose, a suitable substrate is made available in a first step. Because the light conduction within the liquid optical waveguide to be created depends predominantly on the coating yet to be applied, so that the substrate plays a minor role for the light conduction, a multiplicity of substrates are in principle possible for the apparatus of the invention. However, upon filling with the liquid to be analyzed and possibly also during the measurement there occur in the liquid optical waveguide high pressures which can be in the order of magnitude of several bars. Hence, there is preferably made available a substrate possessing an accordingly sufficient mechanical stability. Materials to be used for the substrate are therefore in particular quartz glass, borosilicate glasses such as Pyrex glass, soda-lime glass, different polycarbonates and, particularly preferably, silicon, for example a silicon wafer.

In a further step, there is applied to the substrate surface by for example lithographic means an etching mask which defines the microchannel to be formed. The material of the etching mask is coordinated with the etching medium and the substrate. For etching a silicon substrate in an acidic environment, for example, nitride is a suitable material for the etching mask.

In a further step, the etching medium acts on the substrate at the points specified by the etching mask. The etching medium is gaseous or liquid and flows on the substrate surface to be etched at a uniform flow velocity during the etching step. In other words, the flow velocity remains constant in time at each point on the surface of the substrate during the etching step, whereby different flow velocities can occur at different points of the substrate. Thus, a high reproducibility of the etched microchannel is attained. Manufacturing the microchannel by etching according to the invention has the advantage, in comparison to milled or embossed microchannels, that it creates surfaces of high quality, that is, smooth surfaces with low surface roughness, in the microchannel, thereby improving the light conduction in the liquid optical waveguide to be created.

Preferably, the etching in the substrate is isotropic, that is, the etching velocity is substantially the same in all spatial directions and independent for example of the crystallographic planes in a silicon wafer. Thus, because of the uniform flow velocity of the etching medium, there can advantageously be created a microchannel with a substantially semi-circular cross section whose depth is equal to or only slightly smaller than half of its width. The depth of the microchannel here is the distance between the plane of the substrate surface and the deepest point of the microchannel on a sectional line extending perpendicular to the longitudinal direction of the microchannel. The depth is measured along the surface normal of the substrate surface. The width of the microchannel is the distance between the intersection points of the microchannel's inner walls with the substrate surface along a sectional line extending perpendicular to the longitudinal direction of the microchannel. The width is measured in the plane of the substrate surface. The ratio between width and depth of the etched microchannel, that is, the aspect ratio of the microchannel, can be influenced in targeted fashion by the flow velocity of the etching medium. Such a semi-circular microchannel is, on the one hand, advantageous for the light conduction in the later liquid optical waveguide and, on the other hand, permits the realization of a simple axial coupling in and out of light by means of an optical waveguide. The microchannel preferably has a depth in the range between 50 and 500 µm, in particular 200, 250, 300, 400 or 500 µm, whereby each of the stated single values can represent a boundary of the stated values range. With such dimensions of the microchannel a laminar liquid flow can be realized in good approximation in the later liquid optical waveguide, meaning that turbulences in the liquid that disturb the spectroscopic analysis are avoided. Further, the microchannel has an altogether small total volume despite a great channel length because of the small channel cross section, so that the minimum amount of a sample liquid to be analyzed is small. The channel lengths preferably amount to more than 1, 2, 3, 5, 10, 15, 20, 25 or 30 meters.

Preferably, the etching medium flows substantially in the direction of the microchannel to be etched. This makes it possible to create a microchannel with a semi-circular cross section, that is, a microchannel whose width and depth are substantially identical.

If the substrate employed is a silicon single crystal, for example a silicon wafer, the latter can in principle be etched with an acidic as well as with an alkaline medium. Upon etching in an alkaline environment, however, the crystal structure plays a great role and the etch shape is defined by special crystal faces ({111} etch stop areas). Thus, with an etching in an alkaline environment an isotropic etching is impossible, as is a partially curved course of the microchannel. In an acidic environment, however, the etching is largely independent of the crystal structure. It is thus possible to realize an isotropic etching which permits the forming of an at least substantially semi-circular microchannel, and the course of the at least partially curved microchannel on the substrate surface can also be chosen at will, in particular independently of the crystal structure of the silicon crystal.

In a preferred embodiment of the manufacturing method of the invention, the substrate to be etched is of circular-disk-shaped configuration, as is the case for example with a silicon wafer. If during the etching step a stir bar conically tapered on both sides or a discus-shaped stir disk is positioned centrally, above the substrate surface to be etched, and rotated, this makes it possible to realize in simple fashion a laminar, uniform and homogeneous flow of the etching medium on the surface of the substrate to be etched. The flow velocity is preferably radially homogeneous, meaning that in at least a given radial region on the substrate surface the etching medium flows in the azimuthal direction, so that the flow velocity of the etching medium is identical at different radii. In other words, in the given radial region the rotational velocity of the etching medium is indirectly proportional to the respective radius. In this connection, "centrally" means that the axis of rotation and symmetry of the stir bar or stir disk is a surface normal of the circular-disk-shaped substrate and extends through the center of the circular-disk-shaped substrate. Further, the microchannel to be etched preferably extends on such a circular-disk-shaped substrate substantially in the azimuthal direction with regard to the center of the circular-disk-shaped substrate. Thus, there is produced with the above-described stirring arrangement during the etching step a laminar, uniform and radially homogeneous flow of the etching medium, said flow going substantially in the direction of the microchannel to be etched. The microchannel to be etched is preferably of spiral-shaped configuration, whereby the center of the spiral coincides at least substantially with the center of the circular disk. Particularly preferably, it is an Archimedean spiral, wherein the radius of the spiral arm, that is, of the microchannel, is proportional to the azimuthal angle.

In a preferred embodiment of the microchannel manufacturing method of the invention, the acting of the etching medium takes place in several steps. Therebetween the etching is interrupted and the substrate with the applied etching mask is rinsed with a suitable substance, for example with water. Such a stepwise etching has the advantage that the etching mask has higher stability during the etching and thus a microchannel of high quality and depth can be created. Preferably, there is employed for each etching step a fresh, completely unspent, optionally newly prepared etching medium.

After etching, the etching mask is removed. Before the microchannel is closed, the inner wall of the microchannel can be smoothed by being polished using gaseous hydrofluoric acid and gaseous ozone.

Subsequently, the etched and optionally polished microchannel is closed. For this purpose, in a first preferred embodiment of the method, the etched microchannel is covered with a planar cover plate. Subsequently, the cover plate is fastened to the substrate, and the etched microchannel thereby closed, thereby forming a closed microchannel. The materials of substrate and cover plate can be identical or also be different. For example, a planar cover plate of quartz glass can be fastened by anodic bonding to a substrate of silicon, for example to a silicon wafer. Alternatively, the cover plate can also itself consist of silicon and be for example a further silicon wafer which is fastened to the etched silicon wafer by means of silicon-silicon direct bonding (SDB). Other materials and combinations of materials can also be connected mechanically by bonding or other bonding processes. Alternatively, all fastening methods are suitable that create a sufficiently mechanically stable connection between substrate and cover plate and at the same time create a sufficient liquid- and light-tightness of the closed microchannel. In anodic bonding, substrate and cover plate are brought to a high temperature, for example 500° C., and a high voltage, for example 1 kV, is applied between substrate and cover plate.

In a further step, the closed channel is provided with a low-refractive coating. Preferably, the coating consists of Teflon, nanoporous silicon dioxide or a nanoporous double compound of magnesium fluoride-magnesium oxyhydroxide. The coating material is dissolved in a suitable solvent, for example FC40, FC75 or FC77, and the solution injected into the closed microchannel. For this purpose, there is introduced into the closed microchannel for example a suitably formed cannula which suitably distributes within the closed microchannel the solution with the coating material to be applied. Subsequently, the closed microchannel is flushed with gaseous nitrogen.

There is thereby created a closed, coated microchannel which is hollow on the inside and forms a liquid optical waveguide when filled with a suitable liquid having a higher refractive index than the low-refractive coating, for example water. The closed microchannel is completely lined with the low-refractive coating.

In an alternative embodiment of the method for creating a closed, coated microchannel, the substrate surface having the etched microchannel and the surface of the planar cover plate are provided with a low-refractive coating before substrate and cover plate are joined. Preferably, the coating consists of Teflon, nanoporous silicon dioxide or a nanoporous double compound of magnesium fluoride-magnesium oxyhydroxide. For this purpose, a solution having the coating material to be applied is applied to the substrate surface having the etched microchannel and the surface of the planar cover plate, for example by spin coating or spray coating. Spin coating, also referred to as rotation coating, is a method for applying thin and uniform layers or films to a substrate. It is suited for applying basically any materials present in solution. The substrate, for example a silicon wafer, is fixed on a turntable and rotated at a certain speed and for a certain time. A metering device above the center of the rotating substrate is used to apply a desired amount of the solution, whereby the solution is distributed uniformly over the substrate surface and excess solution is spun off. Preferably, the solution is applied in several steps and the substrate is heated between these steps, so that the solvent evaporates and the optionally nanoporous structure of the coating forms. In spray coating, there is produced a fine mist of a solvent having coating material dissolved therein, which is deposited on the substrate surface having the etched microchannel and the surface of the planar cover plate. After the evaporation of the solvent the coating material previously dissolved in the solvent remains on the surface. Preferably, the spray coating is also done in several steps, for example in four steps, between which the substrate is rotated by 90° and heated.

Subsequently, the substrate is covered with the planar cover plate, so that the respective low-refractive coatings of the substrate surface and the planar cover plate come to lie one on the other. Subsequently, substrate and cover plate are stuck together by heating substrate and cover plate. In so doing, the substrate and cover plate, in particular when using Teflon as a coating material, are heated above the glass temperature but not above the destruction temperature of the coating material. Thus, the two low-refractive coatings connect with each other, and there again arises a closed microchannel that is completely lined with a low-refractive coating.

Further embodiment examples and advantages of the invention will be explained hereinafter by way of example with reference to the accompanying figures. The examples represent preferred embodiments which in no way limit the invention. The shown figures are schematic representations that do not reflect the real proportions, but serve to improve the clearness of the different embodiment examples.

Figure 2:
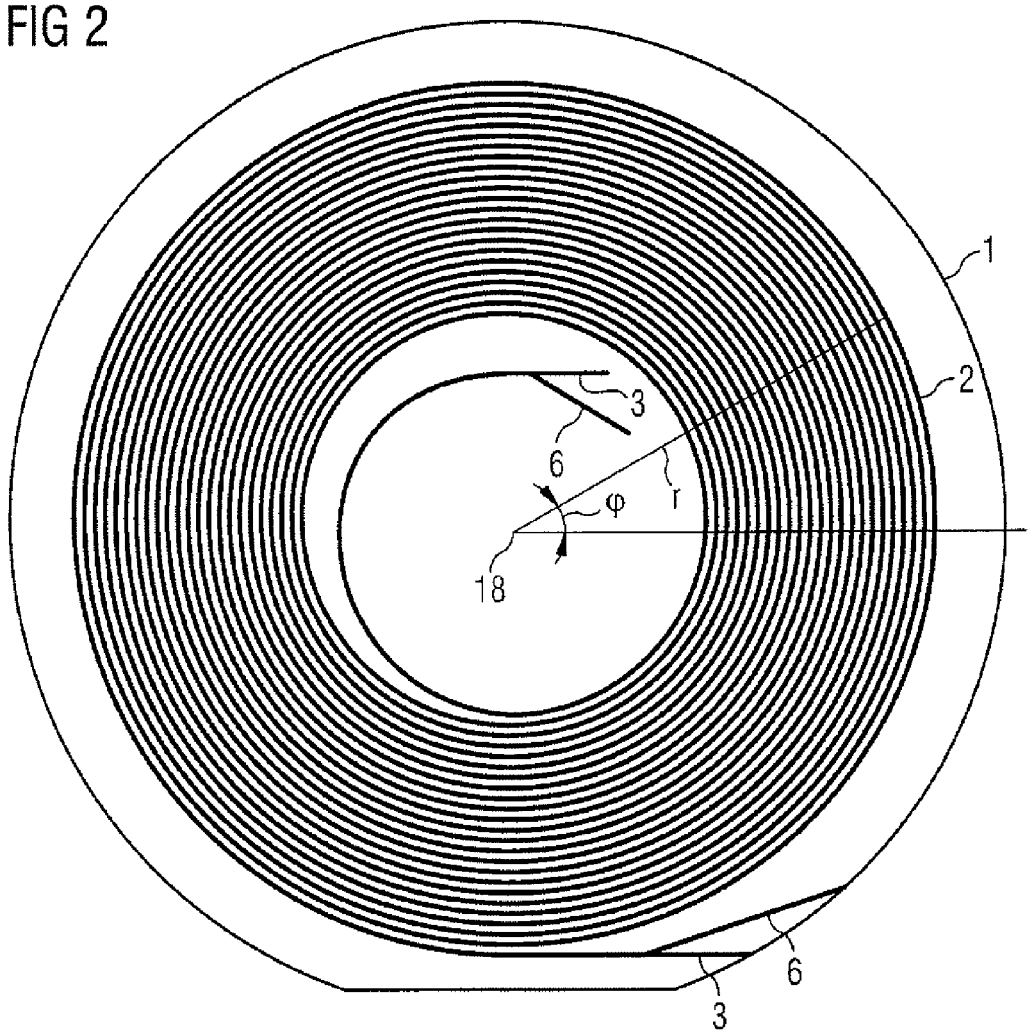
Figure 3:
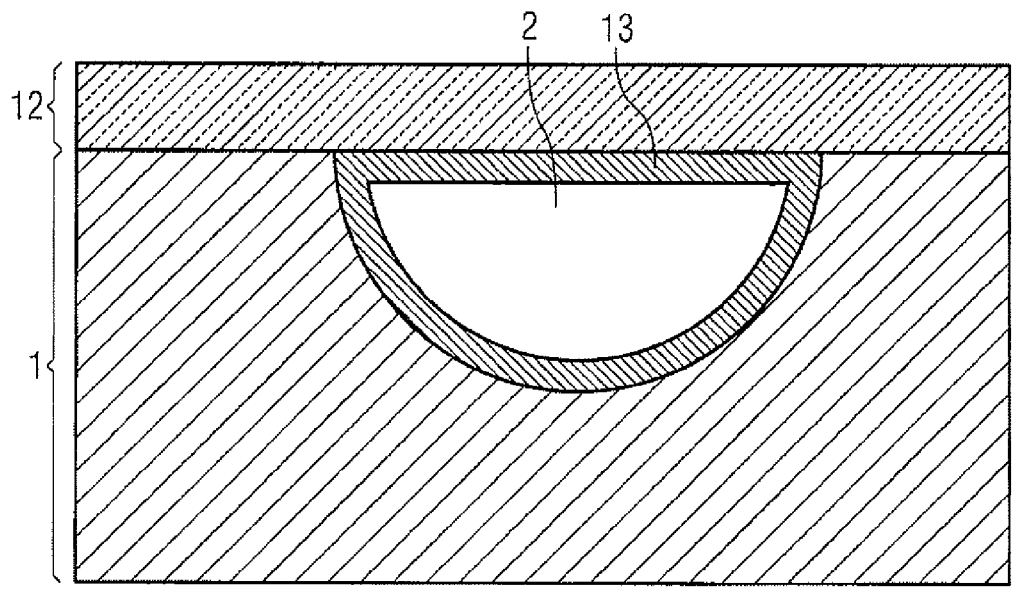
Figure 4:
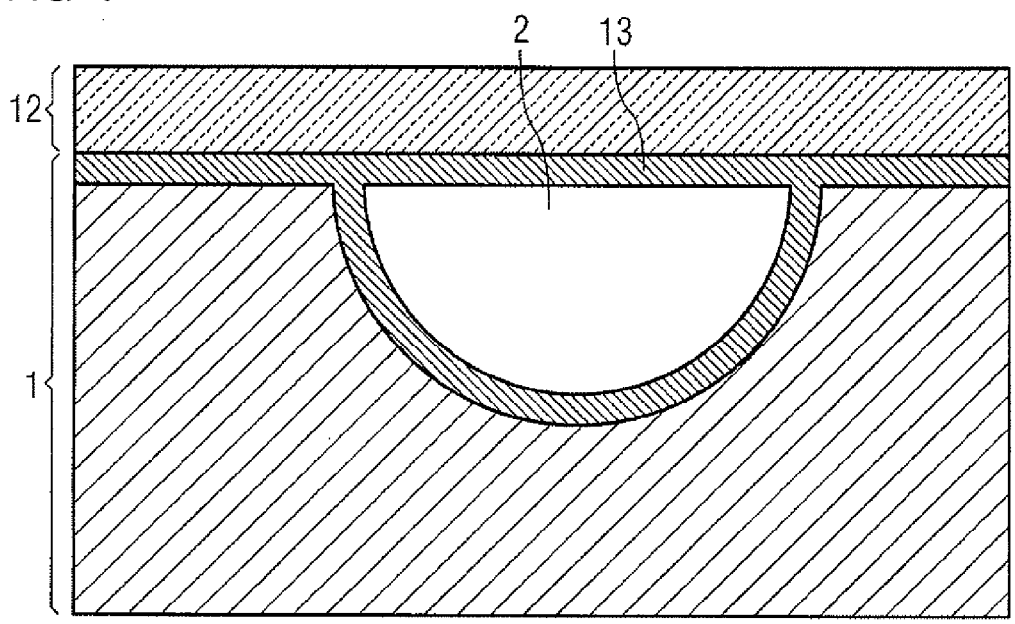
Figure 5:
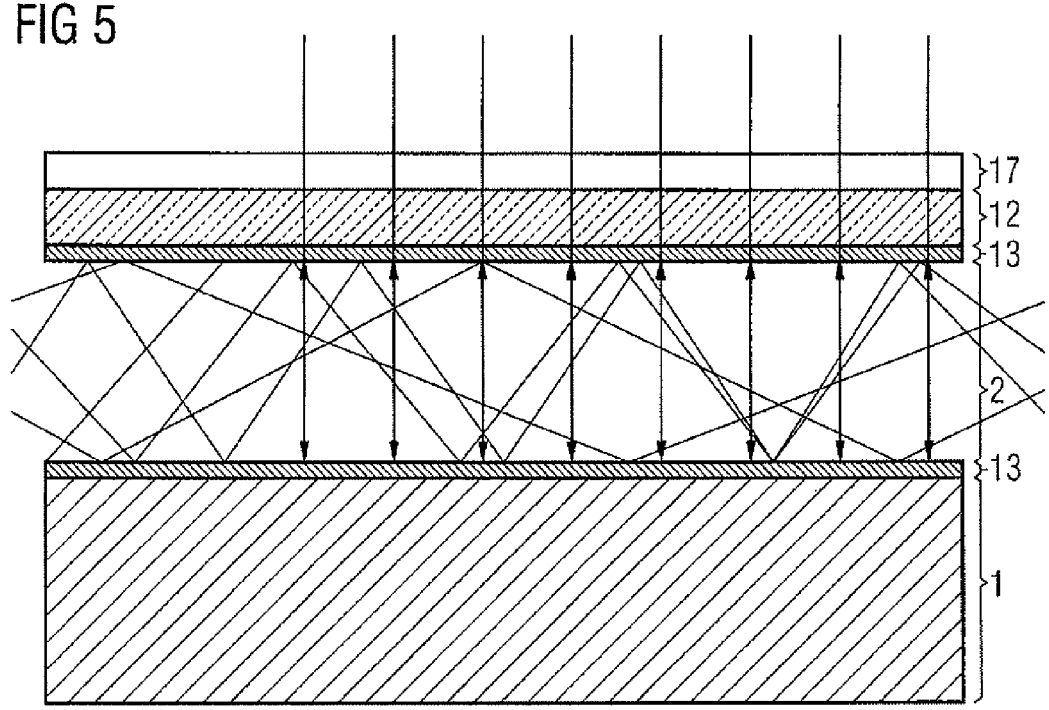
Figure 6:
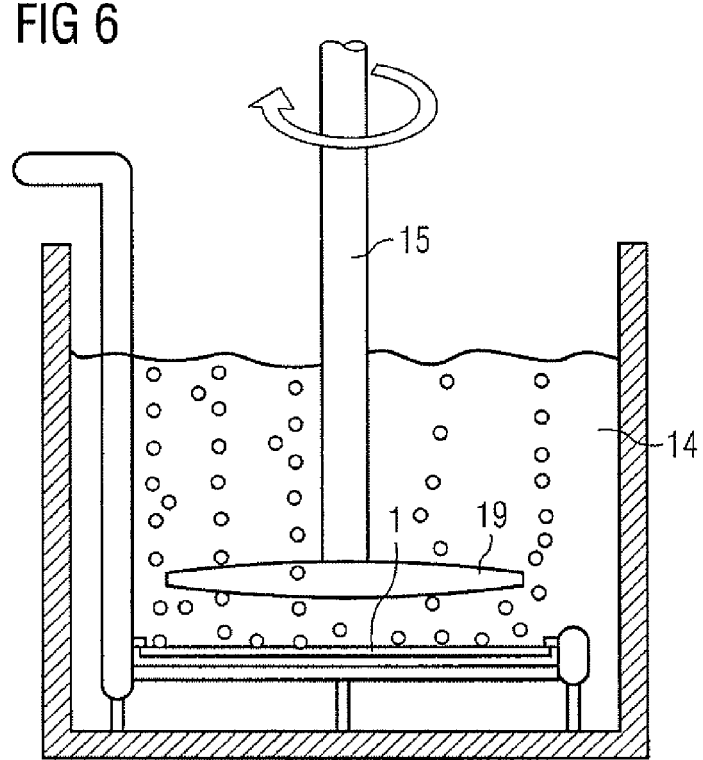
Figure 7:
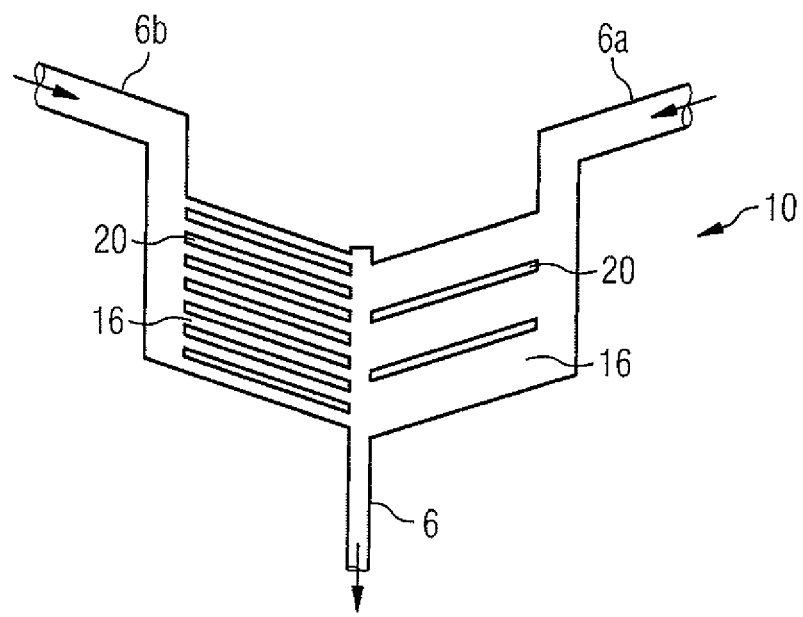

Specifically, the figures show:

FIG. 1 a schematic view of the measuring apparatus;
FIG. 2 a plan view of a spiral-shaped liquid optical waveguide;
FIG. 3 a cross section through a first embodiment example of a coated, closed microchannel;
FIG. 4 a cross section through a second embodiment example of a coated, closed microchannel;
FIG. 5 a longitudinal section through a measuring apparatus for fluorescence measurement;
FIG. 6 an arrangement for etching a silicon substrate;
FIG. 7 a first embodiment example of a micromixer; and
FIG. 8 a second embodiment examples of a micromixer.

In FIG. 1 there is schematically represented an embodiment example of a measuring apparatus. A spiral-shaped microchannel 2 is formed here on a circular-disk-shaped silicon wafer 1. The microchannel is coated with Teflon in the embodiment example and, upon supplying of an aqueous solution, forms a liquid optical waveguide 2. Alternatively, the microchannel can be coated with a nanoporous silicon dioxide or magnesium fluoride-magnesium oxyhydroxide. The microchannel 2 is covered with a cover plate not represented in FIG. 1, so that there results a hermetically closed microchannel which is light- and liquid-tight. The measuring apparatus further comprises a monochromatic light source 4, a light detector 5 and optical waveguides 3 which permit an axial coupling in and out of light in the closed microchannel. Thus, on the one hand, the monochromatic visible light of the light source 4 can be coupled axially into the liquid optical waveguide and, on the other hand, the transmitted light can be coupled axially out of the liquid optical waveguide 2 and supplied to the light detector 5. This allows absorption measurements and transmission measurements to be performed in the liquid optical waveguide 2. As a light detector, an avalanche diode is employed. Alternatively, other types of photodiodes or other suitable light detectors can also be employed. In particular, there can also be provided a spectral filtering (by wavelength filter or by spectrometric methods) that precedes the light detection. If the requirements for miniaturization are less high, light sources and/or light detectors with greater dimensions can also be employed, which are connected optically to the liquid optical waveguide via for example self-supporting optical waveguides 3. Between the liquid optical waveguide 2 and the optical waveguides 3 there are provided microlenses (not represented), for example GRIN (gradient-index) lenses, to increase by their small aperture the yield of light coupled in and out.

Liquid is supplied to the liquid optical waveguide and removed via feed lines 6, 6a, 6b. In so doing, a sample liquid 7 and a detection liquid 8 are respectively pumped into the feed line 6 via micropumps 9. Sample liquid 7 and detection liquid 8 are mixed in a predetermined mix ratio in the micromixer 10 before being fed to the liquid optical waveguide 2, whereby micromixer 10 and micropumps 9 are represented separately from the silicon wafer 1 in FIG. 1. In an alternative embodiment, however, the micropumps 9, the micromixer 10 and the corresponding feed lines 6, 6a, 6b are integrated on the silicon wafer 1, which leads to a considerable miniaturization of the total measuring apparatus. In the measuring apparatus the spectroscopic absorption measurements and transmission measurements can be performed with the liquid still or flowing within the liquid optical waveguide 2. The removed liquid is collected in a collecting vessel 11 and can subsequently be discarded.

In the measuring apparatus represented in FIG. 1 there is the possibility of mixing two liquids in a predetermined mix ratio before they are fed to the liquid optical waveguide. Thus, there can be detected for example metal ions in the sample liquid 7. These metal ions frequently have absorption bands in the low UV range, which is not readily accessible to absorption measurements and transmission measurements. An exception is for example the $Ni^{2+}$ ion, which in aqueous solution shows an absorption at 670 nm which can be employed for detecting such $Ni^{2+}$ ions. The sample liquid 7 having the metal ions dissolved in aqueous solution is mixed with the detection liquid 8 in which a suitable complexing agent is dissolved in likewise aqueous solution. The complexing agent enters into a coordination compound with the metal ion, whereby the resulting complex possesses allowed charge-transfer transitions which possess a high extinction coefficient ($\epsilon$>1000) and lie in the visible spectral range. For example, $Cu^{2+}$ ions form with the complexing agent 1,10-phenanthroline ($C_{12}H_8N_2$) an ionic complex having one copper ion and three 1,10-phenanthroline molecules ($[Cu(C_{12}H_8N_2)_3]^{2+}$), which possesses a characteristic absorption band at 650 nm. With the same complexing agent there can also be detected $Fe^{2+}$ ions, which form with 1,10-phenanthroline an ionic complex of one Fe ion and three 1,10-phenanthroline molecules ($[Fe(C_{12}H_8N_2)_3]^{2+}$), which possesses a characteristic absorption band at 510 nm. $Fe^{2+}$ ions can also form with the anion of 3-(2-pyridyl)-5,6-bis(4-phenyl-sulfonic acid)-1,2,4-triazine-5',5"-disodium salt $[C_{16}H_8N_4O_8S_2]^{2-}$ a complex $[Fe(C_{16}H_8N_4O_8S_2)_3]^{4-}$), which possesses a characteristic absorption at 567 nm.

The use of complexes for detecting metal ions has, on the one hand, the advantage that the characteristic absorption of the formed complex lies in the visible spectral range. This makes it possible to employ as a light source light-emitting diodes (LEDs) or semiconductor lasers, which are available as cost-efficient components with small dimensions and can emit monochromatic light in the visible wavelength range. The monochromatic light is typically sufficiently narrow-band so that the total light can be employed for the absorption measurement without previous spectral filtering and be detected by a light detector without further spectral filtering. Therefore, both as a light source and as a light detector there can be employed components with small outer dimensions which can advantageously be arranged directly on the silicon wafer or a cover plate lying thereover. Thus, it is possible, in sum, to integrate on the substrate a multiplicity of the apparatuses necessary for feeding liquids and light, thereby substantially miniaturizing the measuring apparatus.

The use of complexing agents for detecting metal ions has the advantage that characteristic absorption bands in the visible spectral range are created. Above all, their extinction is considerably stronger than the extinction of the metal ions themselves. Thus, the detection limit for metal ions can be significantly lowered. The detection limit can also be considerably lowered by the great channel length of the microchannel 2 and the resulting long light path within the liquid optical waveguide 2. Altogether, measurements in the sub-ppb range are thus possible.

The embodiment example represented in FIG. 1 permits a miniaturized construction of a measuring apparatus which nevertheless makes great optical path lengths available and thus makes low detection limits possible. The detection limit is lowered further by the additional employment of suitable detection reactions.

In the embodiment example represented in FIG. 1 there is employed as a substrate a four-inch silicon wafer in which a microchannel is etched with a depth of 250 μm. The microchannel is covered with a light-transmissive, planar cover plate of quartz glass (not represented). The microchannel is coated with a 3 μm thick coating of Teflon, so that the closed and coated microchannel 2 forms a liquid optical waveguide 2 for aqueous solutions.

In FIG. 2 the silicon wafer 1 is represented with a greater degree of detail. The spiral-shaped microchannel 2, apart from the end areas, is configured as an Archimedean spiral, that is, the radius r of the microchannel 2 changes linearly with the azimuthal angle φ of the spiral, starting from the center 18 (center of symmetry) of the spiral. The spiral has a pitch of 600 μm. The pitch is the change of the radius r of the spiral-shaped microchannel 2 after passing an azimuthal angle φ of 2π. This guarantees a great total length of the microchannel and of the corresponding liquid optical waveguide. In the shown embodiment example, the length of the liquid optical waveguide amounts to approx. 4.7 meters.

As to be seen in FIG. 2, the microchannel 2 is not continued to the center 18 of the spiral, since light losses increasingly occur at an increasing radius of curvature of such a liquid optical waveguide, since the angle of incidence of light on the boundary surface between the liquid core of the liquid optical waveguide and the low-refractive coating becomes greater and thus the total reflection condition is satisfied by a smaller proportion of the light. In other words, the proportion of modes affected by light loss in the liquid optical waveguide 2 increases. Hence, in the embodiment example represented in FIG. 2, the spiral of the microchannel 2 is guided on the four-inch silicon wafer disk only up to a minimum spiral radius of 1 cm. Thereafter, the light is coupled out of the liquid optical waveguide 2. Light losses on account of the radius of curvature of the liquid optical waveguide can be reduced by applying the low-refractive, totally reflective coating in the microchannel 2 to a highly reflective substrate 1. Such a highly reflective surface can be obtained employing silicon as a substrate, because silicon is metallically reflective. Further, it is advantageous in this connection when the microchannel possesses a smooth surface, as is obtained for example upon etching, in particular upon wet-chemical etching of such a silicon substrate. Alternatively, the light losses can also be reduced upon small radii of curvature when a totally reflective coating with an especially small refractive index is employed. This can be obtained by employing nanoporous silicon dioxide or magnesium fluoride-magnesium oxyhydroxide.

As represented schematically in FIG. 2, light is axially coupled in and out of the liquid optical waveguide for example via waveguides 3. Further, liquid is supplied to the liquid optical waveguide and removed therefrom via feed lines 6. As to be seen in FIG. 2, the feed lines 6 show an angle of 30° relative to the longitudinal axis of the microchannel 2. This ensures a laminar flow within the liquid optical waveguide. Alternatively, other angles between feed line and longitudinal axis of the liquid optical waveguide can also be chosen in dependence on the chosen hydraulic conditions within the liquid optical waveguide.

In FIGS. 3 and 4 there is represented a cross section through the microchannel 2. In both figures the microchannel is hermetically closed by a transparent cover plate 12 of for example quartz glass. Further, the microchannel 2 is completely lined with a totally reflective, low-refractive layer. The closed microchannel represented in FIG. 3 was manufactured by fastening the quartz glass cover plate 12 to the silicon substrate 1 by anodic bonding. Subsequently, Teflon was injected into the closed microchannel and flushed with gaseous nitrogen, so that the closed microchannel 2 is enclosed completely by a totally reflective Teflon layer 13 having a layer thickness of 3 μm. By the anodic bonding there is created a closed microchannel which is sufficiently liquid- and light-tight to form a liquid optical waveguide.

The closed and coated microchannel represented in FIG. 4 was manufactured by a manufacturing method alternative thereto. Here, the quartz glass cover plate 12 and the etched silicon substrate 1 were first coated with Teflon by the spin coating method or spray coating method. Subsequently, the substrate 1 and the cover plate 12 were placed with the coated sides one on the other and the total arrangement was heated to a temperature of 330° C. Therefore, the Teflon coatings of substrate 1 and cover plate 12 stick together beside the etched microchannel 2 and there likewise arises, in sum, a closed microchannel 2 which is completely surrounded by a totally reflective layer 13 and is sufficiently liquid- and light-tight to form a liquid optical waveguide.

In FIG. 5 there is represented a longitudinal section through a measuring apparatus for fluorescence measurements. Here, excitation light, for example UV light, is coupled into the liquid optical waveguide 2 transversally through a quartz glass cover plate 12 (coming from above in the figure). In the liquid contained in the liquid optical waveguide 2 there is produced fluorescence light which is totally reflected on the low-refractive layer 13 and conducted to the ends of the liquid optical waveguide 2. The cover plate 12 is provided with a coating 17 that is anti-reflective in the UV range, in order to minimize losses through reflection upon the transversal coupling in of the excitation light. To increase the yield of fluorescence light of the substance to be detected, the substance can be labeled with fluorescent dyes beforehand and subsequently measured. The represented measuring apparatus can alternatively be employed for Raman measurements, where the excitation light typically lies in the visible spectral range. The anti-reflective coating 17 then acts anti-reflectively in the visible spectral range.

In FIG. 6 there is schematically represented an embodiment example of an apparatus setup for the etching of a silicon substrate 1. Here, a circular-disk-shaped silicon wafer 1 with a diameter of four inches is subjected to an etching solution 14. Etching takes place in an acidic environment and the etching solution contains acids such as hydrofluoric acid, acetic acid, nitric acid and/or hydrogen peroxide in suitable proportions, optionally with surfactant. In this liquid etching solution 14 the silicon wafer 1 to be etched is fastened in a suitable etching container with the process side upward. The back side of the silicon wafer 1 located below is passivated. The represented upward arrangement of the process side of the silicon wafer 1 has the advantage that any gases arising upon etching can escape easily. Two centimeters above the circular-disk-shaped silicon wafer 1, a rotationally symmetric stirrer 15 having a conical stir bar or a discus-shaped stir disk 19 is positioned centrally and rotated. This realizes a laminar flow within the etching solution, resulting in a uniform, homogeneous flow velocity of the etching medium on the wafer surface. Such a laminar, homogeneous flow optimizes the etching velocity, because spent etching solution is continuously removed at every point of the wafer surface. The etching temperature here should be within the diffusion-controlled region. Accordingly, the etching velocities in the vertical direction, that is, perpendicularly to the wafer surface, and the horizontal direction, that is, along the wafer surface, are substantially equal, thereby achieving in good approximation an isotropic etching and a microchannel 2 with an accordingly semi-circular cross section. Such a semi-circular cross section is represented schematically in FIGS. 3 and 4. Further, the laminar, uniform flow on the process surface of the silicon wafer guarantees a circular and smooth etched trench and thus a microchannel 2 with a smooth surface and low surface roughness.

For additionally smoothing the surface of the microchannel, the microchannel can be treated, when required, with a gas mixture of hydrofluoric acid and ozone. In so doing, the gas is distributed over the total wafer uniformly via a nozzle array. This resulting removal by polishing amounts to 1-2 μm.

In the represented embodiment example, the etching of the microchannel 2 is done in several steps. For example, each etching step lasts four minutes. Subsequently, the silicon wafer 1 is removed from the etching solution 14 and rinsed with water. Subsequently, the silicon wafer is inserted into the etching solution 14 again, a laminar flow of the etching solution 14 produced by means of the stirrer 15 again, and a further etching step carried out with a predetermined duration and fresh, newly prepared etching solution for example once more for four minutes. Such a sequential etching in several etching steps, which are interrupted by rinsing of the silicon wafer, improves the durability of the etching mask, which consists of nitride in this embodiment example. Thus, an uncontrolled widening is largely avoided, and there is obtained a microchannel of high quality.

In FIG. 7 there is represented a micromixer which is integrated on the silicon wafer 1. The micromixer 10 allows two liquids which respectively flow via the feed lines 6a and 6b to be effectively mixed and to be supplied to the liquid optical waveguide 2 via feed lines 6. The feed lines 6a and 6b can be dimensioned in accordance with the planned application, but are represented with an identical diameter in FIG. 7. Because no turbulences are generally present in microchannels, there would not occur any flow-induced mixture of the two liquids (sample liquid 7 and detection liquid 8) upon simple merging of the feed lines 6a and 6b into a common feed line 6.

In the micromixer represented in FIG. 7, the ends of the feed lines 6a and 6b form the input channels of the micromixer 10, and the beginning of the feed line 6 the output channel of the micromixer 10. In FIG. 7, the input channels and the output channel are arranged parallel. However, they can alternatively also be arranged at an angle to each other. The two input channels and the output channel are respectively connected via a multiplicity of parallel flow channels 16 which are arranged at a non-right angle to the input channels and the output channel. Neighboring flow channels 16 are respectively separated mutually by lamellae 20. The flow channels have a length between 100 and 1000 μm and a width between 20 and 500 μm.

The micromixer does not necessarily possess a symmetric construction. It can rather be optimized to the planned application and for this purpose be constructed differently on each side, that is, in the part serving to feed the sample liquid 7 and in the part serving to feed the detection liquid 8. In particular, different lengths and/or different widths of the parallel flow channels can be provided on each side.

In the embodiment example represented in FIG. 7, the lengths of the flow channels are identical on each side and amount respectively to 1000 μm. On the side represented on the left in FIG. 7, which serves to feed the detection liquid 8 via the feed line 6b, the flow channels have a width of 50 μm. On the side represented on the right in FIG. 7, which serves to feed the sample liquid 7 via the feed line 6a, the flow channels 16 have a width of 500 μm. At the same width of the lamellae 20 separating the flow channels 16 of 100 μm, the right side (sample liquid 7) of the micromixer 10, in the represented embodiment example, has in the region between the input channel and the central output channel a lower number of flow channels 16, an accordingly lower number of lamellae 20 and thus an altogether higher cross section of flow than the corresponding left side (detection liquid 8) of the micromixer. Thus, the micromixer 10 represented in FIG. 7 favors a mix ratio of the resulting liquid mixture with a greater proportion of sample liquid 7 and a smaller proportion of detection liquid 8. The mix ratio is further influenced by the pumps provided in the feed lines 6a and 6b.

Figure 8:
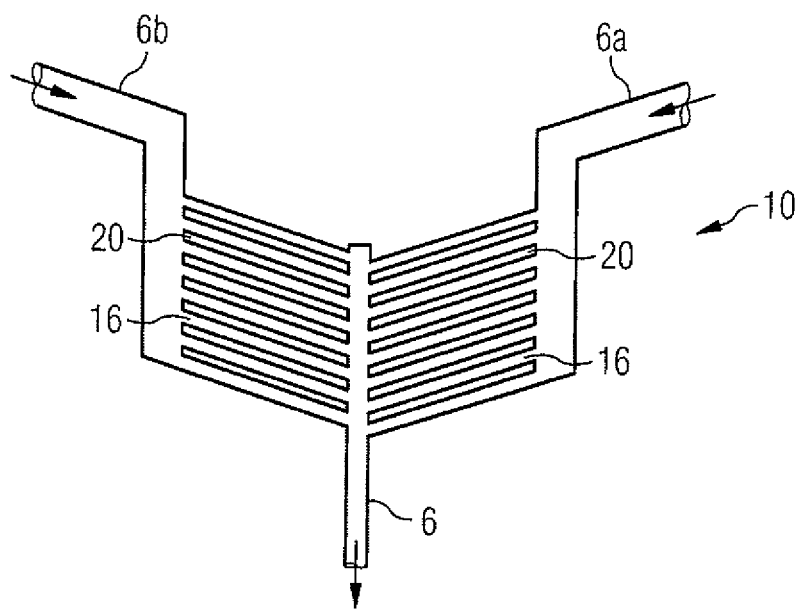

In the second embodiment example of the micromixer 10 represented in FIG. 8, the two sides of the micromixer are constructed identically. The length of the flow channels 16 amounts here to 200 μm and the width of the flow channels 16 amounts to 50 μm. The width of the lamellae amounts to 20 μm and the length of the lamellae is equal to the length of the flow channels. Further, the flow channels 16 are arranged mutually offset on the left and right sides of the micromixer 10, so that the ends of the flow channels 16 respectively oppose the end face of a lamella. This construction of the micromixer 10 produces in the output channel small-dimensioned layer stacks of the two liquids to be mixed, which mix quickly by diffusion. This effect also occurs in the first embodiment example of the micromixer 10 represented in FIG. 7.

The micromixers represented in FIGS. 7 and 8 thus guarantee an effective intermixing of two different liquids without employing turbulences.

The invention claimed is:

1. A measuring apparatus comprising:
an apparatus for forming a liquid optical waveguide comprising a silicon wafer as a substrate (1) having an isotropically etched, spiral-shaped microchannel (2) which is provided with a coating (13) that is low-refractive in comparison with an aqueous solution, and which is covered with a cover plate (12) for forming a closed microchannel (2), whereby the cover plate (12) is provided with a further low-refractive coating (13) at least above the microchannel (2), whereby there is formed in the substrate (1) at least one feed line (6) which permits a supplying of liquid into the closed microchannel (2) and/or a removing of liquid from the closed microchannel (2), whereby a respective feed line (6) is preferably formed at the ends of the microchannel (2), and whereby there is provided at least at one end of the closed microchannel (2), preferably at both ends of the microchannel (2), an apparatus for coupling light axially into the closed microchannel and/or for coupling light axially out of the closed microchannel (2), as well as
a light source (4) which is adapted to penetrate the closed microchannel (2) with light,
a light detector (5), and
a first liquid pump (9) which supplies a sample liquid (7) to the closed microchannel (2) via the at least one feed line (6, 6a).

2. The measuring apparatus according to claim 1, characterized in that the measuring apparatus is adapted to provide a continuous liquid stream within the microchannel.

3. The measuring apparatus according to claim 1 or 2, characterized in that the apparatus for forming a liquid optical waveguide for axially coupling light in and/or out is configured as a receiving means for an optical waveguide (6) which permits a coupling in and/or coupling out via the optical waveguide (6), whereby the receiving means is preferably configured as an axial, straight continuation of the microchannel within the substrate (1).

4. The measuring apparatus of claim 1, characterized in that the cover plate (12) is light-transmissive, preferably consists of quartz glass and is particularly preferably provided with a coating (17) that is anti-reflective in the UV and VIS spectral ranges.

5. The measuring apparatus of claim 1, characterized in that a micromixer (10) and/or a micropump (9) is formed in the at least one feed line (6).

6. The measuring apparatus according to claim 5, further comprising:
a second liquid pump (9) which supplies a detection liquid (8) to the closed microchannel (2) via a micromixer (10).

7. The measuring apparatus according to any of claims 1, 2, 4, 5, or 6, further comprising:
a first optical waveguide (3) which is adapted to couple light of the light source (4) axially into the closed microchannel (2) at a first end of the closed microchannel (2), whereby the light source (4) is preferably adapted to emit monochromatic, visible light, and/or
a second optical waveguide (3) which is adapted to couple light axially out of the closed microchannel (2) at a second end of the closed microchannel (2) and to feed it to the light detector (11).

8. A measuring method for the measuring apparatus of claims 1, 2, 4, 5, or 6, the measuring method, comprising the steps of:
supplying sample liquid (7) and preferably detection liquid (8) into the closed microchannel (2),
transversally penetrating the closed microchannel (2) with light of the light source (4), which is preferably configured as an excitation light source,
axially coupling light out of the closed microchannel (2),
detecting the coupled-out light in the light detector (11).

9. A measuring method for the measuring apparatus of claims 1, 2, 4, 5, or 6, the measuring method, comprising the steps of:
supplying sample liquid (7) and preferably detection liquid (8) into the closed microchannel (2),
coupling light of the light source (4) axially into the closed microchannel (2) at one end of the closed microchannel (2),
coupling transmitted light axially out of the closed microchannel (2) at another end of the closed microchannel (2),
detecting the transmitted light in the light detector (11).

10. The measuring method of claim 8, characterized in that a continuous liquid stream is provided within the microchannel.

11. An apparatus for forming a liquid optical waveguide comprising a silicon wafer as a substrate (1) having an isotropically etched, spiral-shaped microchannel (2) which is provided with a coating (13) that is low-refractive in comparison with an aqueous solution, and which is covered with a cover plate (12) for forming a closed microchannel (2), whereby the cover plate (12) is provided with a further low-refractive coating (13) at least above the microchannel (2).

12. The apparatus according to claim 11, characterized in that there is formed in the substrate (1) at least one feed line (6) which permits a supplying of liquid into the closed microchannel (2) and/or a removing of liquid from the closed microchannel (2), whereby a respective feed line (6) is preferably formed at the ends of the microchannel (2).

13. The apparatus of claims 11 or 12, characterized in that at least at one end of the closed microchannel (2), preferably at both ends of the microchannel (2), there is provided an apparatus for coupling light axially into the closed microchannel and/or for coupling light axially out of the closed microchannel (2).

14. The apparatus according to claim 13, characterized in that the apparatus for coupling light axially in and/or out is configured as a receiving means for an optical waveguide (6), which permits a coupling in and/or out via the optical waveguide (6), whereby the receiving means is preferably configured as an axial, straight continuation of the microchannel within the substrate (1).

15. The apparatus of claims 11 or 12, characterized in that the cover plate (12) is light-transmissive, preferably consists of quartz glass and is particularly preferably provided with a coating (17) that is anti-reflective in the UV and VIS spectral ranges.

16. The apparatus of claim 12, characterized in that a micromixer (10) and/or a micropump (9) is formed in the at least one feed line (6).

* * * * *